(12) United States Patent
Li et al.

(10) Patent No.: US 7,552,649 B1
(45) Date of Patent: Jun. 30, 2009

(54) CABLE TESTING DEVICE

(75) Inventors: Wu-Gao Li, Tu-Cheng (TW); Yi Zhang, Tu-Cheng (TW)

(73) Assignee: Cheng Uei Precision Industry Co., Ltd., Taipei Hsien (TW)

( * ) Notice: Subject to any disclaimer, the term of this patent is extended or adjusted under 35 U.S.C. 154(b) by 0 days.

(21) Appl. No.: 12/181,657

(22) Filed: Jul. 29, 2008

(51) Int. Cl.
*G01N 3/08* (2006.01)

(52) U.S. Cl. ....................................................... 73/829

(58) Field of Classification Search ................... 73/829, 73/862, 453; 254/277
See application file for complete search history.

(56) References Cited

U.S. PATENT DOCUMENTS

| | | | |
|---|---|---|---|
| 1,851,895 A * | 3/1932 | Cornet | 73/829 |
| 2,092,439 A * | 9/1937 | Bouhuys | 73/829 |
| 5,520,369 A * | 5/1996 | Chatard | 254/277 |
| 6,926,260 B1 * | 8/2005 | De Groot et al. | 254/277 |
| 7,151,322 B2 * | 12/2006 | Eskandr | 290/1 R |

* cited by examiner

*Primary Examiner*—Lisa M Caputo
*Assistant Examiner*—Octavia Davis
(74) *Attorney, Agent, or Firm*—Muncy, Geissler, Olds & Lowe, PLLC

(57) ABSTRACT

A cable testing device adapted for testing a resisting conical-rotation ability of a cable includes a clipping apparatus for clipping one end of the cable, a rotatable apparatus disposed below the clipping apparatus and driven to rotate round an axis thereof, a first inverting member positioned at the rotatable apparatus and apart from the axis of the rotatable apparatus, a second inverting member positioned at the rotatable apparatus and being in substantially vertical line with the axis of the rotatable apparatus, and a connecting member. One end of the connecting member is connected with the cable. The other end of the connecting member sequentially detours the first inverting member and the second inverting member to be tied to a weight freely drooping with a barycenter thereof lying in line with the axis of the rotatable apparatus.

9 Claims, 4 Drawing Sheets

CABLE TESTING DEVICE

BACKGROUND OF THE INVENTION

1. Field of the Invention

The present invention generally relates to a cable testing device, and more particularly to a cable testing device capable of testing a resisting conical-rotation ability of a cable.

2. The Related Art

Traditionally, in the course of a cable being in use, the cable is usually connected with a plug. When the plug is fixed in an electronic device, the cable is apt to rotate round the junction of the cable and the plug with a certain angle. The rotating orbit of the cable is conical-shaped approximately. When the cable frequently does a conical-rotation, interior conductors of the cable (such as wires, braid etc.) are apt to be broken at the junction of the cable and the plug. Thus, it is necessary to test a resisting conical-rotation ability of the cable.

Referring to FIG. 5, a traditional cable testing device adapted for testing a resisting conical-rotation ability of a cable 3' is shown. The cable testing device includes a rotatable apparatus 1', a clipping apparatus 2', a driving apparatus (not shown) and a control system (not shown). The rotatable apparatus 1' is levelly disposed on the driving apparatus controlled by the control system. The clipping apparatus 2' is located above the rotatable apparatus 1' for clipping one end of the cable 3'. One end of a spring 7 is connected with the cable 3' and the other end thereof is connected to one edge of the rotatable apparatus 1'. The control system has two signal outputs respectively connected with interior conductors of the cable 3' in series to form a circuit.

In use, the clipping apparatus 2' is adjusted to position the cable 3' at an angle of 45 degrees with respect to the rotatable apparatus 1'. Then the control system controls the driving apparatus to drive the rotatable apparatus 1' and the cable 3' to rotate periodically and reciprocally. When the interior conductors of the cable 3' are broken, the two signal outputs of the control system are in a broken circuit so that the control system controls the driving apparatus and further controls the rotatable apparatus 1' to stop rotating. At this moment, a result of the resisting conical-rotation ability of the cable 3' can be gotten according to the rotating times of the rotatable apparatus 1' shown on the control system.

The foregoing cable testing device tests the resisting conical-rotation ability of the cable 3' by way of the spring 7 connecting with the cable 3' and the rotatable apparatus 1' so as to produce a pulling force acting on the cable 3'. However, when the rotatable apparatus 1' accelerates or decelerates in the process of rotating, the pulling force is apt to be changed. Furthermore, after the spring 7 and the cable 3' rotate periodically and reciprocally for a long time, the spring 7 and the cable 3' are apt to fatigue to result in the length thereof lengthening, thereby the pulling force acting on the cable 3' is reduced. Therefore, the result gotten by the above-mentioned cable testing device is not accurate enough.

SUMMARY OF THE INVENTION

An object of the present invention is to provide a cable testing device adapted for testing a resisting conical-rotation ability of a cable. The cable testing device includes a clipping apparatus for clipping one end of the cable, a rotatable apparatus disposed below the clipping apparatus and driven to rotate round an axis thereof, a first inverting means positioned at the rotatable apparatus and apart from the axis of the rotatable apparatus, a second inverting means positioned at the rotatable apparatus and being in substantially vertical line with the axis of the rotatable apparatus, and a connecting member. One end of the connecting member is connected with the cable. The other end of the connecting member sequentially detours the first inverting means and the second inverting means to be tied to a weight freely drooping with a barycenter thereof lying in line with the axis of the rotatable apparatus.

As described above, the cable testing device defines the first inverting means and the second inverting means, after the connecting member sequentially detours the first inverting means and the second inverting means to be tied to the weight, the weight freely droops to produce a pulling force acting on the cable. Therefore, even if the rotatable apparatus accelerates and decelerates or the cable and the connecting member become fatigued during testing, the pulling force of the weight acting on the cable keeps constant. Therefore, the cable testing device of the present invention can more accurately test the resisting conical-rotation ability of the cable.

BRIEF DESCRIPTION OF THE DRAWINGS

The present invention will be apparent to those skilled in the art by reading the following description of a preferred embodiment thereof, with reference to the attached drawings, in which.

DETAILED DESCRIPTION OF THE PREFERRED EMBODIMENT

Figure 1:
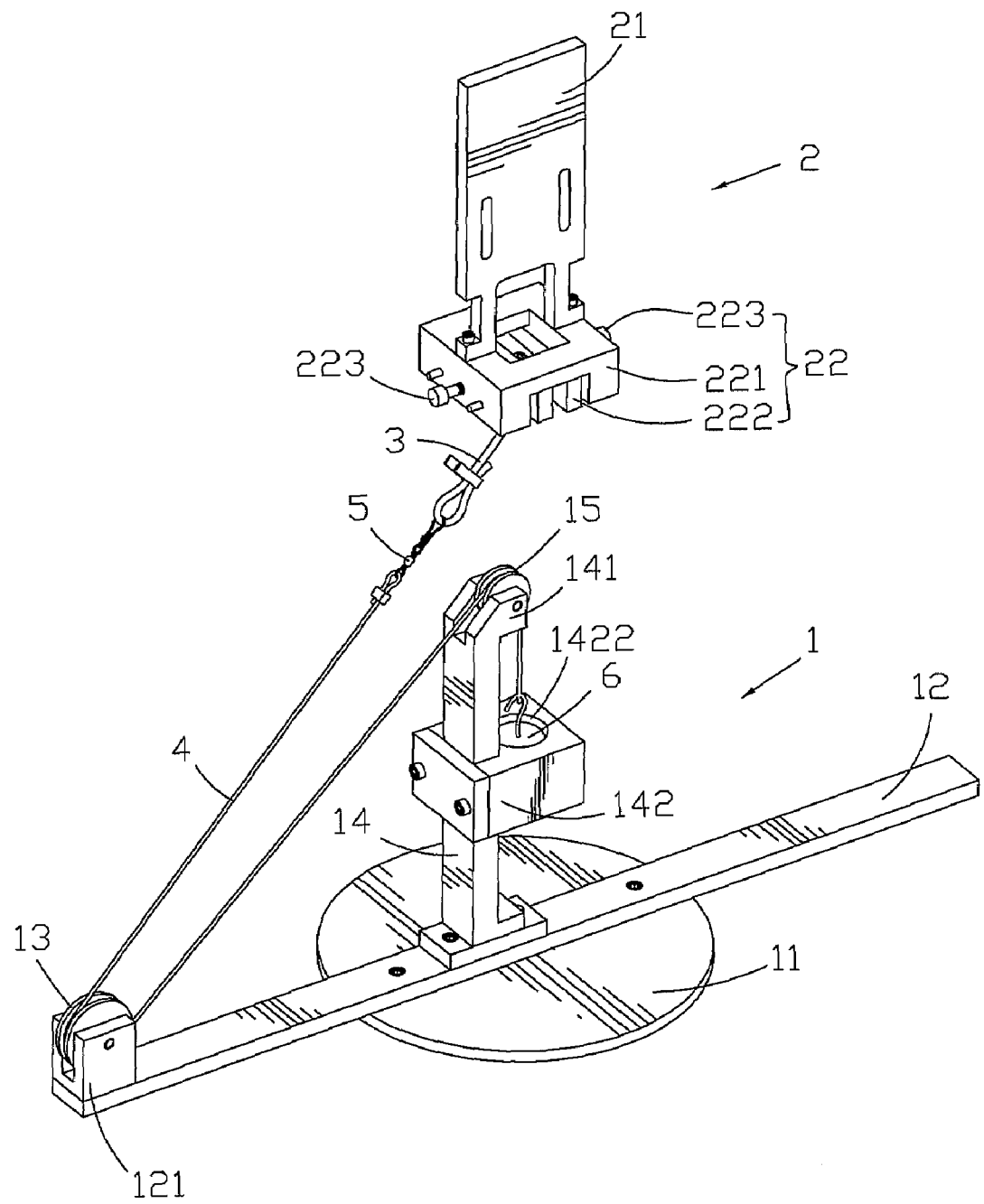
FIG. 1 is a perspective view of a cable testing device according to the present invention.
Figure 2:
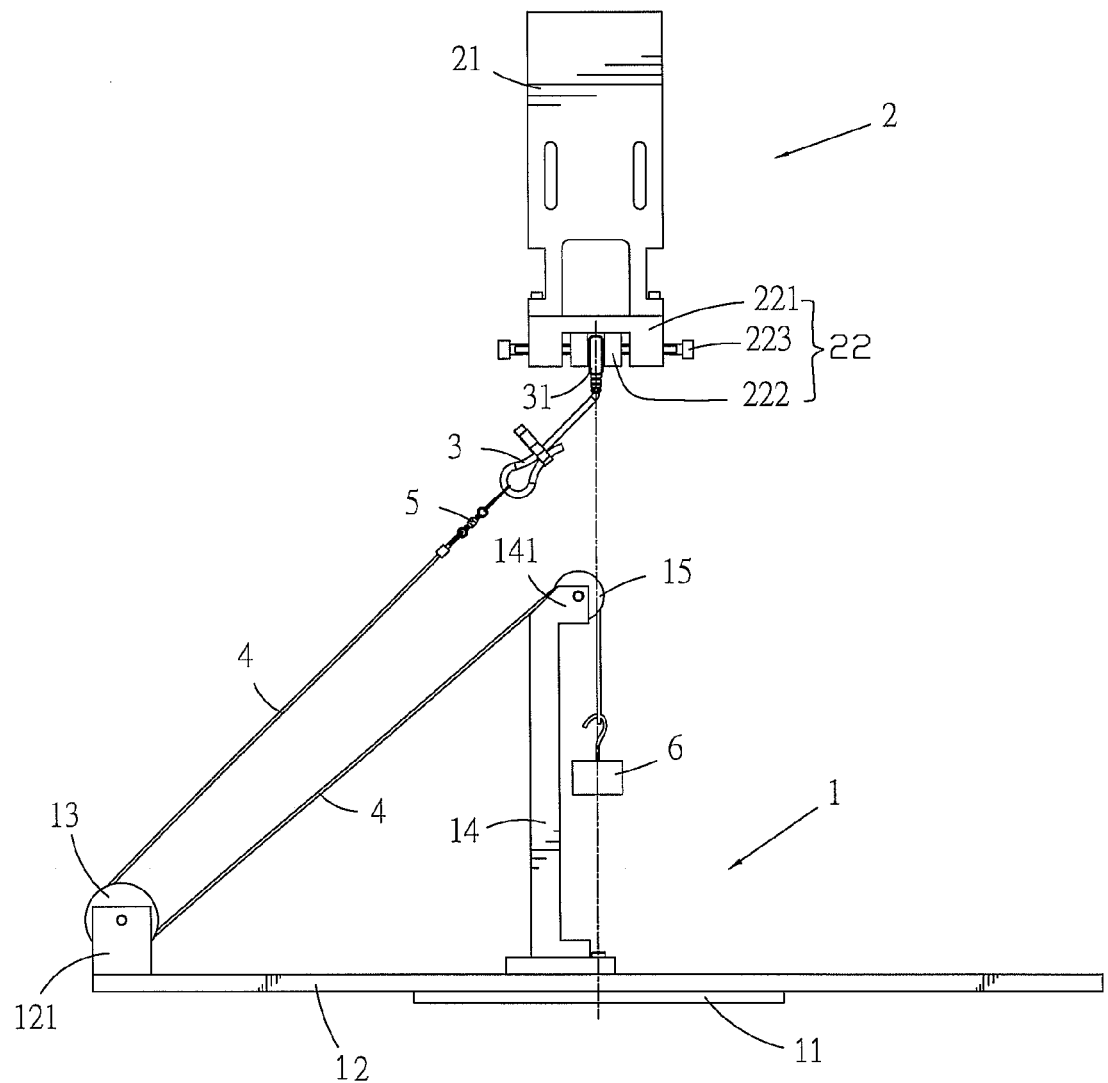
FIG. 2 is a front view of the cable testing device of FIG. 1, wherein a fixing block of a rotatable apparatus is removed.

With reference to FIGS. 1 and 2, a cable testing device in accordance with the present invention is shown to test a resisting conical-rotation ability of a cable 3, wherein the cable 3 includes two wires and a braid (not shown) and one end of the cable 3 is connected with a plug 31. The cable testing device of the present invention includes a rotatable apparatus 1, a clipping apparatus 2, a connecting member (not labeled), a driving apparatus (not shown), a control system (not shown) and a base frame (not shown). The rotatable apparatus 1, the clipping apparatus 2, the driving apparatus and the control system are mounted to the base frame.

The rotatable apparatus 1 includes a disc-shaped base plate 11, a horizontal support 12, a vertical support 14 and a fixing block 142. The base plate 11 is levelly fixed on the driving apparatus which is controlled by the control system, thereby the control system can control the driving apparatus to rotate the base plate 11 with an axis of the base plate 11. The horizontal support 12 is of rectangular bar shape and fixed on a top of the base plate 11. The center of the horizontal support 12 is in line with the axis of the base plate 11, and two ends of the horizontal support 12 respectively stretch beyond the base plate 11. One end of the horizontal support 12 protrudes upward to form a U-shaped first holder 121 for pivoting a first inverting means therein. The pivot of the first inverting means is parallel with the width direction of the horizontal support 12. In this embodiment, the first inverting means is a first fixed pulley 13. The vertical support 14 extends vertically and is fixed on the approximate middle of the top of the horizontal support 12. The top of the vertical support 14 extends horizontally away from the first holder 121 to form a second holder 141 for pivoting a second inverting means therein. The second inverting means is coplanar with the first inverting means and the horizontal support 12. In this embodiment, the second inverting means is a second fixed pulley 15. The fixing block 142 is of rectangular shape and fixed to the middle of the vertical support 14. The fixing block 142 defines a cylindrical perforation 1422 penetrating from top to bottom thereof. The axis of the perforation 1422 is in line with the axis of the base plate 11.

Figure 3:
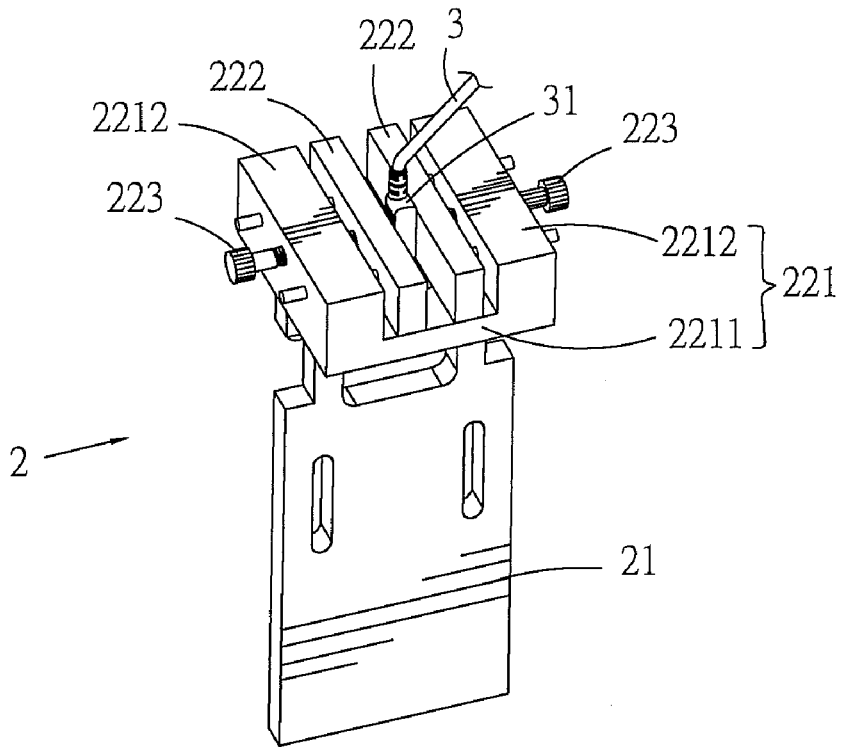
FIG. 3 is a perspective view of a clipping apparatus of the cable testing device of FIG. 1.

Referring to FIGS. 1, 2 and 3, the clipping apparatus 2 being located above the second fixed pulley 15 includes a fixing body 21 and a clipping body 22. The fixing body 21 is of rectangular board shape in substance and vertically fixed on the base frame. The clipping body 22 includes a holding block 221, two slides 222 and two adjusting screws 223. The holding block 221 has a rectangular base section 2211 being fixed on the bottom of the fixing body 21. Two opposite ends of the base section 2211 respectively extend downward to form a sidewall 2212. The two slides 222 which are rectangular are movably mounted between the two sidewalls 2212 and parallel with the two sidewalls 2212. The two adjusting screws 223 are rotatably mounted in the middle of the respective sidewalls 2212. The adjusting screw 223 passes through the corresponding sidewall 2212 and is fastened in the respective slide 222. Therefore, the two slides 222 can be adjusted to slide close or away from each other by way of rotating the respective adjusting screws 223.

Figure 4:
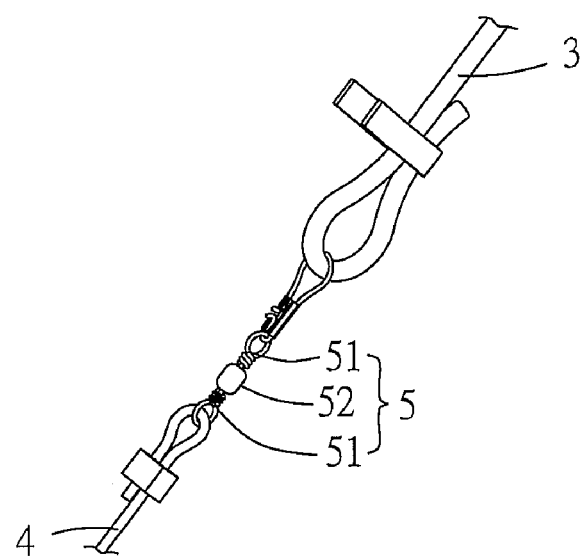
FIG. 4 is a perspective view of a connecting chain of the cable testing device of FIG. 1, wherein the connecting chain connects with a cable and a string.
Figure 5:
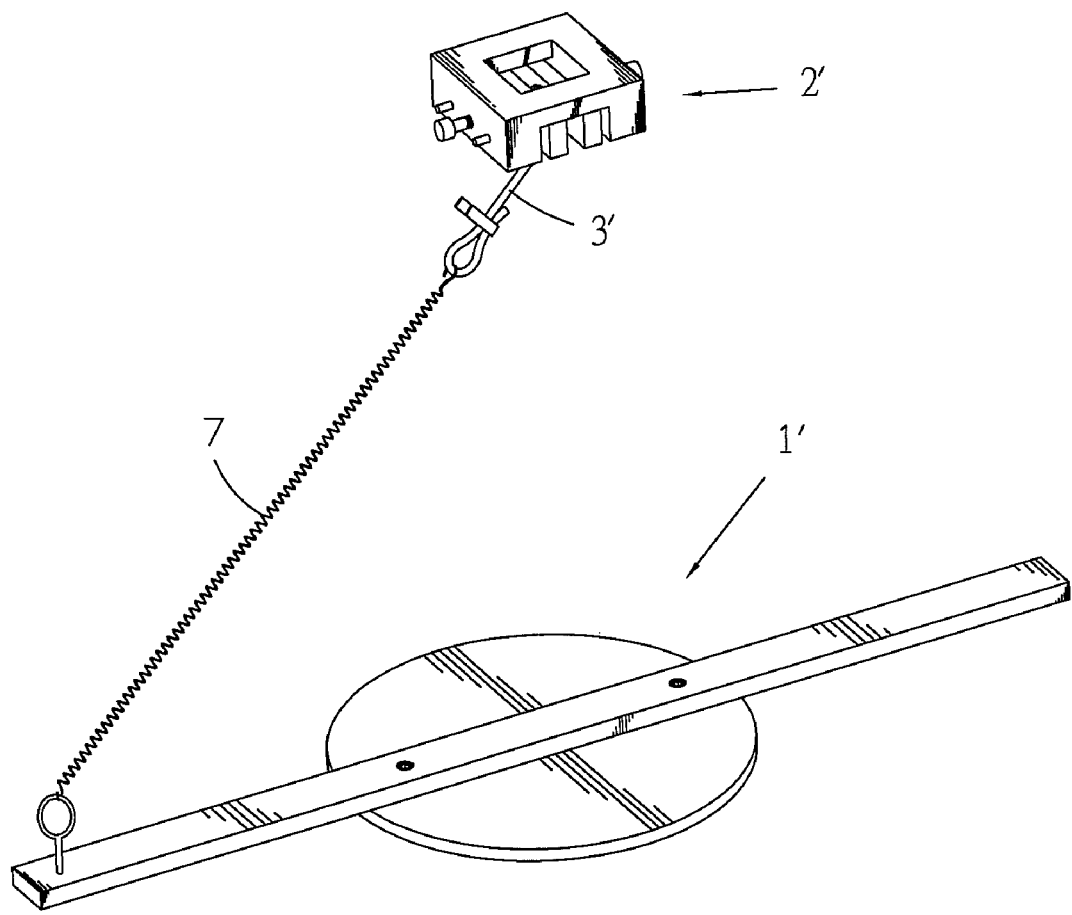
FIG. 5 is a perspective view of a traditional cable testing device.

Referring to FIG. 1, FIG. 2 and FIG. 4, in use, the two slides 222 of the clipping apparatus 2 are appropriately adjusted by rotating the respective adjusting screws 223 to firmly clip the plug 31 therebetween and ensure that the junction of the plug 31 and the cable 3 lies in line with the axis of the base plate 11 of the rotatable apparatus 1. The connecting member includes a string 4 and a connecting chain 5. The connecting chain 5 is used to connect with the cable 3 and the string 4. The connecting chain 5 includes two connecting ropes 51 and a receiving bead 52. One end of one connecting rope 51 is connected with the cable 3 and the other end thereof is rotatably received in the receiving bead 52. One end of the other connecting rope 51 is connected with one end of the string 4 and the other end thereof is rotatably received in the receiving bead 52. The other end of the string 4 sequentially detours the bottom of the first fixed pulley 13 and the top of the second fixed pulley 15 to freely hang above the perforation 1422 of the fixing block 142 and be tied to a weight 6. The weight 6 freely droops to produce a pulling force acting on the string 4 and the cable 3 and is received in the perforation 1422, thereby the fixing block 142 prevents the weight 6 from rocking freely during the rotatable apparatus 1 rotating. The barycenter of the weight 6 is in line with the axis of the base plate 11. At last, adjust the clipping apparatus 2 to position the cable 3 at an angle of 45 degrees with respect to the horizontal support 12. The control system controlling the driving apparatus has two signal outputs respectively connected with the wires and the braid of the cable 3 in series to form a circuit for testing whether the wires and the braid are broken or not during testing the resisting conical-rotation ability of the cable 3 and for showing the rotating times of the rotatable apparatus 1 until the cable 3 is broken.

The control system is preset in an appropriate condition to control the driving apparatus before starting the cable testing device. Generally, the control system controls the driving apparatus to drive the rotatable apparatus 1 in a periodical and reciprocal rotation such that to clockwise rotate the rotatable apparatus 1 at 720 degrees and then counterclockwise rotate at 720 degrees. In the process of the rotatable apparatus 1 rotating, when the wires or the braid of the cable 3 is broken under the action of the repeated torsion, the two signal outputs of the control system are in a broken circuit, thereby the control system controls the driving apparatus and further controls the rotatable apparatus 1 to stop rotating. At this moment, a result of the resisting conical-rotation ability of the cable 3 can be gotten according to the rotating times of the rotatable apparatus 1 shown on the control system.

As described above, the cable testing device defines the first fixed pulley 13 and the second fixed pulley 15, after the string 4 detours the bottom of the first fixed pulley 13 and the top of the second fixed pulley 15 to be tied to the weight 6, the weight 6 freely droops to produce the pulling force acting on the cable 3 and is received in the perforation 1422 of the fixing block 142. Therefore, even if the rotatable apparatus 1 accelerates and decelerates or the cable 3 and the string 4 become fatigued during testing, the pulling force of the weight 6 acting on the cable 3 keeps constant. Furthermore, the cable 3 and the string 4 are connected by the connecting chain 5 and can rotate at the receiving bead 52 of the connecting chain 5. Hence, the connecting chain 5 can prevent the string 4 from rotating oneself in the process of the rotatable apparatus 1 rotating so as to prevent the weight 6 from rocking freely. Therefore, the cable testing device of the present invention can more accurately test the resisting conical-rotation ability of the cable 3.

What is claimed is:

1. A cable testing device adapted for testing a resisting conical-rotation ability of a cable, comprising:
   a clipping apparatus for clipping one end of the cable;
   a rotatable apparatus disposed below the clipping apparatus and capable of being driven to rotate around an axis thereof;
   a first inverting means positioned at the rotatable apparatus and apart from the axis of the rotatable apparatus;
   a second inverting means positioned at the rotatable apparatus and being in substantially vertical line with the axis of the rotatable apparatus; and
   a connecting member, one end of the connecting member being connected with the cable, the other end of the connecting member sequentially detouring the first inverting means and the second inverting means to be tied to a weight freely drooping with a barycenter thereof lying in line with the axis of the rotatable apparatus.

2. The cable testing device as claimed in claim 1, wherein the clipping apparatus is located above the second inverting means for clipping the cable at a position substantially in line with the axis of the rotatable apparatus.

3. The cable testing device as claimed in claim 1, wherein the first inverting means is a first fixed pulley and the second inverting means is a second fixed pulley.

4. The cable testing device as claimed in claim 3, wherein the first fixed pulley and the second fixed pulley are coplanar with each other, the connecting member sequentially detours a bottom of the first fixed pulley and a top of the second fixed pulley.

5. The cable testing device as claimed in claim 3, wherein the rotatable apparatus includes a base plate disposed levelly, a horizontal support and a vertical support, the horizontal support is levelly fixed on the base plate and defines a first holder at one end thereof, the first fixed pulley is pivoted in the first holder, the vertical support is vertically fixed on the horizontal support and defines a second holder at a top thereof, the second fixed pulley is pivoted in the second holder.

6. The cable testing device as claimed in claim 5, wherein the rotatable apparatus further includes a fixing block fixed to the vertical support, the fixing block defines a perforation vertically extending and lying substantially in line with the axis of the rotatable apparatus, the weight is received in the perforation.

7. The cable testing device as claimed in claim 2, wherein the clipping apparatus includes a fixing body and a clipping body, the clipping body has a holding block, two slides movably mounted in the holding block for clipping the one end of the cable therebetween, and two adjusting screws for adjusting the two slides.

8. The cable testing device as claimed in claim 1, wherein the connecting member includes a string and a connecting chain.

9. The cable testing device as claimed in claim 8, wherein the string is linked with the connecting chain, the connecting chain includes two connecting ropes and a receiving bead, one end of one connecting rope is connected with the cable and the other end thereof is rotatably received in the receiving bead, one end of the other connecting rope is connected with the string and the other end thereof is rotatably received in the receiving bead.

* * * * *